(12) United States Patent    (10) Patent No.: US 10,413,615 B2
Hutchins                     (45) Date of Patent:     Sep. 17, 2019

(54) PROCESS FOR PREPARING CELL-BINDING AGENT-CYTOTOXIC AGENT CONJUGATES

(71) Applicant: IMMUNOGEN, INC., Waltham, MA (US)

(72) Inventor: Benjamin M. Hutchins, Boxborough, MA (US)

(73) Assignee: IMMUNOGEN, INC., Waltham, MA (US)

( * ) Notice: Subject to any disclaimer, the term of this patent is extended or adjusted under 35 U.S.C. 154(b) by 142 days.

(21) Appl. No.: 15/527,525

(22) PCT Filed: Nov. 18, 2015

(86) PCT No.: PCT/US2015/061310
§ 371 (c)(1),
(2) Date: May 17, 2017

(87) PCT Pub. No.: WO2016/081584
PCT Pub. Date: May 26, 2016

(65) Prior Publication Data
US 2017/0354742 A1    Dec. 14, 2017

Related U.S. Application Data

(60) Provisional application No. 62/081,914, filed on Nov. 19, 2014.

(51) Int. Cl.
A61K 47/68    (2017.01)
C07K 16/28    (2006.01)

(52) U.S. Cl.
CPC ...... *A61K 47/6803* (2017.08); *A61K 47/6817* (2017.08); *A61K 47/6889* (2017.08); *C07K 16/28* (2013.01); *C07K 16/2863* (2013.01); *C07K 2317/24* (2013.01)

(58) Field of Classification Search
CPC ............ A61K 47/6803; A61K 47/6889; A61K 47/6817; C07K 16/28; C07K 16/2863; C07K 2317/24
USPC ..................................................... 546/278.4
See application file for complete search history.

(56) References Cited

U.S. PATENT DOCUMENTS

2011/0003969 A1* 1/2011 Kellogg ............... C07K 16/46
                                                  530/303
2012/0282282 A1* 11/2012 Lutz .................. A61K 47/6803
                                                  424/181.1

FOREIGN PATENT DOCUMENTS

WO    2012112687 A1    8/2012
WO    2014134483 A2    9/2014
WO    2014160160 A2    10/2014
WO    WO-2017136623 A1 *  8/2017 ............... C07K 1/13

OTHER PUBLICATIONS

Blanc; Clin Cancer Res 2011, 17, 6448-6458. (Year: 2011).*
Perez; Drug Discovery Today 2014, 19, 869-881. (Year: 2014).*

* cited by examiner

Primary Examiner — Daniel R Carcanague
(74) Attorney, Agent, or Firm — McCarter & English, LLP; Steven G. Davis; Xin Zhang

(57) ABSTRACT

The present invention provides a novel process for preparing a cell-binding agent cytotoxic agent conjugate. The process comprises the steps of: (a) reacting a cytotoxic agent with a bifunctional crosslinking reagent represented by the structural formula (I) or a salt thereof, in a buffer solution comprising a buffering agent to provide a first mixture comprising a cytotoxic agent-linker compound, wherein the buffer solution has high buffer capacity; and (b) reacting the first mixture comprising the cytotoxic agent-linker compound from step (a) with a cell-binding agent in a solution having a pH of 4 to 9 to provide a second mixture comprising the cell-binding agent cytotoxic agent conjugate. The cell-binding agent cytotoxic agent conjugates prepared according to the processes described herein are also included in the present invention.

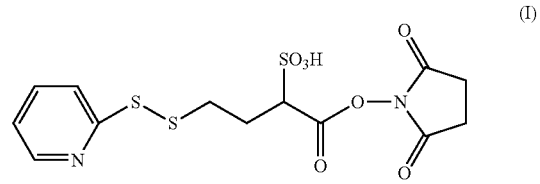

(I)

19 Claims, No Drawings
Specification includes a Sequence Listing.

PROCESS FOR PREPARING CELL-BINDING AGENT-CYTOTOXIC AGENT CONJUGATES

REFERENCE TO RELATED APPLICATIONS

This application is a U.S. national stage filing under 35 U.S.C. § 371 based on International Application PCT/US2015/061310, filed on Nov. 18, 2015, which claims the benefit of the filing date, under 35 U.S.C. § 119(e), of U.S. Provisional Application No. 62/081,914, filed on Nov. 19, 2014. The entire contents of each of the foregoing applications, including all drawings, formulae, specification, claims and sequence listings, are incorporated herein by reference.

BACKGROUND OF THE INVENTION

Antibody-Drug-Conjugates (ADC's) which are useful for the treatment of cancer and other diseases are commonly composed of three distinct elements: a cell-binding agent; a linker; and a cytotoxic agent. The conventional method of conjugating a cell-binding agent, such as an antibody, to a cytotoxic agent, employs two distinct reaction steps. In the first reaction step, the antibody is reacted with a bifunctional crosslinking reagent to produce a linker-modified antibody. The modified antibody product is then optionally purified from the excess linker or hydrolyzed linker reagent. In the second reaction step, the linker-modified antibody is reacted with the cytotoxic agent containing a reactive group, such as thiol, to generate the antibody-cytotoxic agent conjugate, which is again purified in an additional purification step. This conventional method may require two purification steps, which lowers the overall yield and makes the process cumbersome and uneconomical for large scale manufacturing of ADCs.

Alternatively, the cytotoxic agent can first react with the bifunctional crosslinking reagent to form a cytotoxic agent-linker compound, which is then reacted with a cell-binding agent to form the cell-binding agent-cytotoxic agent conjugate (conjugation reaction). The cytotoxic agent, the bifunctional crosslinking reagent and the resulting cytotoxic agent-linker compound are generally hydrophobic compounds and have low solubility in water. As such, a certain amount of organic solvent is required to be present in the conjugation reaction to solubilize the cytotoxic agent-linker compound. On the other hand, the presence of large amount of organic solvent may have a detrimental effect on the antibody stability. Accordingly, the process of the art may be limited to small scale preparation of the cell-binding agent-cytotoxic agent conjugates when low concentrations of cell-binding agents, cytotoxic agents and/or bifunctional crosslinking reagents are used.

In view of the foregoing, there is a need to develop improved processes for preparing cell-binding agent-cytotoxic agent conjugates with high antibody stability and are suitable for large scale productions.

SUMMARY OF THE INVENTION

The present invention provides novel processes that are suitable for large scale production of antibody-drug-conjugates (ADCs). The processes comprise the steps of:

(a) reacting a cytotoxic agent with a bifunctional crosslinking reagent represented by the following structural formula:

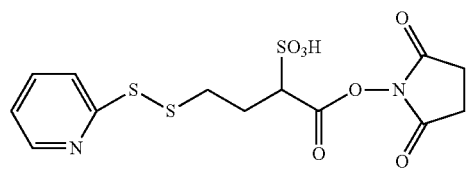 [SMILES: O=C(ON1C(=O)CCC1=O)C(CCSSc1ccccn1)S(=O)(=O)O]

or a salt thereof, in a buffer solution comprising a buffering agent to provide a first mixture comprising a cytotoxic agent-linker compound, wherein the buffer solution has high buffer capacity; and (b) reacting the cytotoxic agent-linker compound in the first mixture from step (a) with a cell-binding agent in a solution having a pH of 4 to 9 to provide the second mixture comprising the cell-binding agent cytotoxic agent conjugate.

It has been surprisingly found that when a high buffer capacity buffer solution is used in the reaction of step (a), the resulting cell-binding agent conjugate has significantly less antibody fragmentation as compared to the conjugates prepared using low buffer capacity buffer solution in the reaction of step (a). In addition, high concentrations of cell-binding agent (e.g., antibody) can be used in the conjugation reaction (i.e., step (b) of the present processes), which makes the process more economical for large-scale production. Moreover, as compared to the process in the art, lower amounts of an organic solvent (e.g., dimethylacetamide (DMA)) are required in the conjugation solution, which may increase the stability of the antibody and the resulting conjugates.

The processes of the present invention provide cell-binding agent cytotoxic agent conjugates with high purity and/or stability. Specifically, the processes of the present invention reduces antibody fragmentation as compared to the processes described in the prior art.

The present invention is also directed to the cell-binding agent cytotoxic agent conjugates prepared using the processes described herein.

DETAILED DESCRIPTION OF THE INVENTION

The present invention provides a novel process for preparing a cell-binding agent cytotoxic agent conjugate. The process comprises the steps of:

(a) reacting a cytotoxic agent with a bifunctional crosslinking reagent represented by the following structural formula:

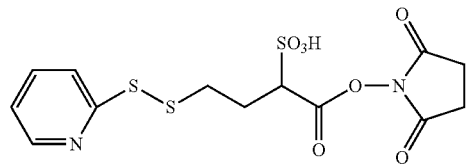

sSPDB or a salt thereof, in a buffer solution comprising a buffering agent to provide a first mixture comprising a cytotoxic agent-linker compound, wherein the buffer solution has high buffer capacity; and (b) reacting the cytotoxic agent-linker compound in the first mixture obtained from step (a) with a cell-binding agent in a solution having a pH of 4 to 9 to provide the second mixture comprising the cell-binding agent cytotoxic agent conjugate.

As used herein, a "salt" refers to a derivative of the compounds described herein wherein the parent compound is modified by making acid or base salts thereof. More specifically, a salt refers to a derivative wherein the parent compound is modified by reacting the parent compound with an inorganic or organic base, such as an alkaline hydroxide or an alkyl amine. In one embodiment, the salt is a sodium salt. Alternatively, the salt is a trialkylammonium salt, e.g., N,N-diisopropylethylammonium salt.

In one embodiment, the cell-binding agent (e.g., an antibody or an antigen binding fragment thereof) is prone to fragmentation. As used herein, "fragmentation" refers to disruption of a covalent bond in a protein (e.g., an antibody). In one embodiment, fragmentation refers to reduction of inter-chain disulfide bonds in the presence of a free thiol. Fragmentation can also includes cleavage of the protein backbone and fragmentation or modification of side chains (see, for example, Vlasak, J. and Ionescu, R. Fragmentation of monoclonal antibodies. mAbs 3:3, 253-263, May/June 2011). Exemplary antibodies or antigen-binding fragments that are prone to fragmentation include, but are not limited to, IgG4, antibodies comprising a lambda light chain, Fab or F(ab')$_2$. Fragmentation can be identified using separation techniques based primarily on the size of the molecule or separation techniques involving the chemistry of amino acid side chains. Separation techniques based primarily on the size of the molecule include, but are not limited to, size-exclusion chromatography (SEC), sodium dodecyl sulfate-polyacrylamide gel electrophoresis (SDS-PAGE) and capillary electrophoresis with SDS (CE-SDS). Separation techniques involving the chemistry of amino acid side chains include, but are not limited to, liquid chromatography, such as reversed-phase HPLC, hydrophobic-interaction HPLC, cation-exchange HPLC, fast protein liquid chromatography (FPLC), ultra performance liquid chromatography (UPLC) and etc.

In certain embodiments, the buffer solution used in step (a) of the present process has high buffer capacity. As used herein, "buffer capacity" refers to the ability of the buffer solution to prevent significant changes in the pH of the reaction mixture in the presence of an added acid or base.

In one embodiment, the buffer solution comprises a molar excess of a buffering agent relative to the bifunctional crosslinking reagent. In another embodiment, the molar ratio of the buffering agent to the bifunctional crosslinking reagent in the buffer solution is from 1.1:1 to 50:1; from 1.2:1 to 30:1; from 1.3:1 to 25:1; or from 1.5:1 to 12.5:1. More specifically, the molar ratio of the buffering agent to the bifunctional crosslinking reagent is from 2:1 to 8:1. Even more specifically, the molar ratio of the buffering agent to the bifunctional crosslinking reagent is from 4:1 to 6:1. In another more specific embodiment, the molar ratio of the buffering agent to the bifunctional crosslinking reagent is 5:1.

In certain embodiments, the buffer solution in step (a) of the present processes has a pH of 4 to 9. More specifically, the pH is from 4.5 to 8.5, 5.0 to 8.5, from 5.5 to 8.5, from 6.0 to 8.5, from 6.5 to 8.5, from 7.0 to 8.5, from 7.1 to 8.5, from 7.2 to 8.5, from 7.3 to 8.5, from 7.4 to 8.5, from 7.5 to 8.5, from 7.5 to 8.4, from 7.5 to 8.3, from 5.0 to 6.5, from 5.0 to 6.0, or from 5.5 to 6.5. In one specific embodiment, the pH is from 7.5 to 8.5 (e.g., 7.5, 7.6, 7.7, 7.8, 7.9, 8.0, 8.1, 8.2, 8.3, 8.4 or 8.5). In another specific embodiment, the pH is from 7.9 to 8.5, 8.0 to 8.4 or 8.1 to 8.3. Even more specifically, the pH is 8.2. Alternatively, the pH is from 4.5 to 5.5 (e.g., 4.5, 4.6, 4.7, 4.8, 4.9, 5.0, 5.1, 5.2, 5.3, 5.4 or 5.5). In another alternative, the pH is from 4.7 to 5.3, 4.8 to 5.2 or 4.9 to 5.1. Even more specifically, the pH is 5.0.

Any suitable buffering agent known in the art can be used. Suitable buffering agents include, for example, but are not limited to, a citrate buffer, an acetate buffer, a succinate buffer, and a phosphate buffer. In one embodiment, the buffering agent is selected from the group consisting of HEPPSO (N-(2-hydroxyethyl)piperazine-N'-(2-hydroxy-propanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), EPPS (4-(2-hydroxyethyl)piperazine-1-propanesulfonic acid), TES (N-[tris(hydroxymethyl)methyl]-2-aminoethanesulfonic acid), MES (2-(N-morpholino)ethanesulfonic acid) and a combination thereof. More specifically, the buffering agent is EPPS.

In certain embodiments, the buffer solution may further comprise an inert salt to maintain the ionic strength of the buffer. In one embodiment, the buffer solution further comprises sodium chloride.

In certain embodiments, the buffer solution of step (a) comprises an organic solvent. More specifically, the organic solvent is dimethylacetamide (DMA). In one embodiment, the buffer solution of step (a) comprise a mixture of water and an organic solvent. More specifically, buffer solution of step (a) comprises a mixture of water and DMA. The organic solvent (e.g., DMA) can be present in the amount of 1%-99%, 5%-99%, 10%-99%, 20%-99%, 30%-99%, 40%-99%, 50%-99%, 60%-99%, 70%-99%, 80%-99%, 90%-99% by volume of the buffer solution. In one embodiment, the organic solvent (e.g., DMA) is present in the amount of 50%-90%, 55%-85%, 60%-80% or 65%-75% by volume of the buffer solution. In a more specific embodiment, the organic solvent (e.g., DMA) is present in the amount of 70% by volume of the buffer solution.

In certain embodiments, molar equivalent amount of the cytotoxic agent and the bifunctional crosslinking reagent is used in the reaction of step (a). In certain embodiments, molar excess of the cytotoxic agent relative to the bifunctional crosslinking reagent is used in the reaction of step (a). In one embodiment, the molar ratio of the cytotoxic agent to the bifunctional crosslinking reagent is from 1.01:1 to 20:1, 1.1:1 to 20:1, from 1.1:1 to 10:1, from 1.1:1 to 5:1, from 1.1:1 to 4:1, from 1.1:1 to 3:1, from 1.1:1 to 2:1, from 1.1:1 to 1.5:1, from 1.1:1 to 1.4:1, or from 1.1:1 to 1.3:1. More specifically, the molar ratio of the cytotoxic agent to the bifunctional crosslinking reagent is 1.2:1.

In certain embodiments, molar excess of the bifunctional crosslinking reagent relative to the cytotoxic agent is used in the reaction of step (a). In one embodiment, the molar ratio of the bifunctional crosslinking reagent to the cytotoxic agent is from 1.01:1, 1.1:1 to 20:1, from 1.1:1 to 10:1, from 1.1:1 to 5:1, from 1.1:1 to 4:1, from 1.1:1 to 3:1, from 1.1:1 to 2:1, from 1.1:1 to 1.5:1, from 1.1:1 to 1.4:1, or from 1.1:1 to 1.3:1.

In certain embodiments, the reaction in step (a) of the present processes is carried out by mixing a cytotoxic agent with the bifunctional crosslinking reagent sSPDB in a buffer solution described above. The reaction is allowed to proceed for 2 minutes to 1 week, 1 hour to 48 hours, 1 hour to 36 hours, 1 hour to 24 hours, 5 hours to 20 hours, 5 hours to 15 hours, 6 hours to 14 hours, 4 hours to 8 hours, 5 hours to 7 hours, 1 hours to 5 hours, 1 hours to 4 hours, 1 hours to 2 hours, or 2 hours to 5 hours. In one embodiment, the reaction is allowed to proceed for 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, etc.

The reaction of step (a) can be carried out at any suitable temperature. In one embodiment, the reaction can be carried out at a temperature from 10° C. to 50° C., from 10° C. to 40° C., or from 10° C. to 30° C. In another embodiment, the reaction can be carried out at a temperature from 15° C. to 25° C., from 16° C. to 24° C., from 17° C. to 23° C., from 18° C. to 22° C. or from 19° C. to 21° C. In yet another embodiment, the reaction can be carried out at 15° C., 16° C., 17° C., 18° C., 19° C., 20° C., 21° C., 22° C., 23° C., 24° C. or 25° C. Alternatively, the reaction can be carried out at a low temperature, such as less than 10° C. or less than 0° C. (provided that the solution is prevented from freezing, e.g., by the presence of an organic solvent used to dissolve the cytotoxic agent and/or the bifunctional crosslinking reagent). In one embodiment, the reaction can be carried out at a temperature from −10° C. to 0° C., from 0° C. to 10° C., or from 0° C. to 5° C.

In certain embodiments, the first mixture obtained from reacting the cytotoxic agent and the bifunctional crosslinking reagent in step (a) of the present processes can be stored for a long period of time (such as for 1 day, 2 days, 3 days, 4 days, 5 days, 6 days, 1 week, 2 weeks, 3 weeks, 1 month, 2 months, 3 months, 4 months, 5 months, 6 months, 1 year, 2 years or 5 years) before reacting with the cell-binding agent. The first mixture can be stored in a frozen state, at a low temperature (e.g., below 10° C., below 5° C. or below 0° C., or at a temperature from −10° C. to 0° C., from 0° C. to 10° C., or from 0° C. to 5° C.). Alternatively, the first mixture can be stored at room temperature or at a temperature from 10° C. to 25° C., from 15° C. to 25° C., or from 20° C. to 25° C. upon completion of the reaction of step (a).

In certain embodiments, the first mixture comprises the cytotoxic agent-linker compound and impurities, such as unreacted cytotoxic agent, unreacted bifunctional crosslinking reagent and reaction by-products, such as hydrolyzed bifunctional crosslinking reagent and/or dimer of the cytotoxic agents.

In certain embodiments, the first reaction mixture is not substantially purified before reacting the cytotoxic agent-linker compound in the first mixture with the cell-binding agent in step (b) of the present processes. As used herein, the term "substantially purified" means that less than 50%, less than 40%, less than 30%, less than 20%, less than 10%, less than 9%, less than 8%, less than 7%, less than 6%, less than 5%, less than 4%, less than 3%, less than 2% or less than 1% of the impurities (such as unreacted cytotoxic agent, unreacted bifunctional crosslinking reagent and reaction by-products, such as hydrolyzed bifunctional crosslinking reagent and/or dimer of the cytotoxic agents) are removed before the cytotoxic agent-linker compound in the first reaction mixture is reacted with the cell-binding agent in step (b) of the present processes.

In certain embodiments, the first mixture obtained from step (a) of the present processes is reacted with a cell-binding agent in a solution (e.g., conjugation buffer solution) having a pH of 4 to 9, 5 to 9, 5.5 to 9, 6 to 9, 6.3 to 9, or 6.3 to 8.7, 6.4 to 8.6, 6.5 to 8.5, 7.3 to 8.7, or 7.4 to 8.6, to provide a second mixture comprising the cell-binding agent cytotoxic agent conjugate. More specifically, the solution has a pH of 7.5 to 8.5 (e.g., 7.5, 7.6, 7.7, 7.8, 7.9, 8.0, 8.1, 8.2, 8.3, 8.4 or 8.5). In another more specific embodiment, the solution has a pH of 7.9 to 8.5, 8.0 to 8.4, or 8.1 to 8.3. In a even more specific embodiment, the solution has a pH of 8.2. In another specific embodiment, the solution has a pH of 6.5 to 7.5 (e.g., 6.5, 6.6, 6.7, 6.8, 6.9, 7.0, 7.1, 7.2, 7.3, 7.4 or 7.5).

In certain embodiments, the solution in step (b) comprises a buffering agent. Any suitable buffering agent known in the art can be used. Suitable buffering agents include, for example, but are not limited to, a citrate buffer, an acetate buffer, a succinate buffer, and a phosphate buffer. In one embodiment, the buffering agent is selected from the group consisting of HEPPSO (N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), EPPS (4-(2-hydroxyethyl)piperazine-1-propanesulfonic acid), TES (N-[tris(hydroxymethyl)methyl]-2-aminoethane-sulfonic acid), MES (2-(N-morpholino)ethanesulfonic acid) and a combination thereof. More specifically, the buffering agent is EPPS. The solution may further comprise an inert salt to maintain the ionic strength of the buffer. In one embodiment, the buffer solution further comprises sodium chloride.

In certain embodiment, the solution of step (b) of the present processes further comprises an organic solvent. More specifically, the organic solvent is dimethylacetamide (DMA). In one embodiment, the solution of step (b) comprises a mixture of water and an organic solvent. More specifically, the solution of step (b) comprises a mixture of water and DMA. The organic solvent (e.g., DMA) can be present in the amount of 1%-99%, 1%-90%, 1%-80%, 1%-70%, 1%-60%, 1%-50%, 1%-40%, 1%-30%, 1%-25%, 2%-20%, 2%-15%, 2%-10%, 2.5%-7.5%, 3%-7%, 4%-6%, or 4.5%-5.5% by volume of the solution. More specifically, the organic solvent (e.g., DMA) is present in the amount of 5% by volume of the solution.

In certain embodiments, in step (b) of the present processes, the first mixture is reacted with a cell-binding agent by adding an aqueous solution comprising the cell-binding agent to the first mixture obtained from step (a) of the present processes. Alternatively, the first mixture obtained from step (a) is added to an aqueous solution comprising the cell-binding agent. In certain embodiments, the first mixture obtained from step (a) is pH adjusted before reacting with the cell-binding agent. In one embodiment, the first mixture is pH adjusted to have a pH equal to the pH of the aqueous solution comprising the cell-binding agent before reacting with the cell-binding agent.

In certain embodiments, the reaction in step (b) is carried out with high concentration of the cell-binding agent. In one embodiment, the concentration for the cell-binding agent in the solution of step (b) is from 5 g/L to 100 g/L. More specifically, the concentration is from 5 g/L to 50 g/L, from 5 g/L to 40 g/L, from 10 g/L to 40 g/L, from 10 g/L to 30 g/L, or from 15 g/L to 25 g/L. In a more specific embodiment, the concentration is from 15 g/L to 25 g/L, from 18 g/L to 22 g/L or from 19 g/L to 21 g/L. In a even more specific embodiment, the concentration is 20 g/L.

In certain embodiments, excess amount of the bifunctional crosslinking reagent relative to the cell-binding agent is used in the processes of the present invention. In one embodiment, the molar ratio of the bifunctional crosslinking reagent to the cell-binding agent is in the range of 1 to 20, 2 to 10, 3 to 8, or 3 to 6. In another embodiment, the molar ratio of the bifunctional crosslinking reagent to the cell-binding agent is 3.5 to 5, e.g., 3.5, 3.6, 3.7, 3.8, 3.9, 4.0, 4.1, 4.2, 4.3, 4.4, 4.5, 4.6, 4.7, 4.8, 4.9, or 5.0.

In certain embodiments, the reaction in step (b) is allowed to proceed for 5 hours to 48 hours, 10 hours to 48 hours, 10 hours to 30 hours, 15 hours to 25 hours. In a specific embodiment, the reaction is step (b) is allowed to proceed for 8 hours to 24 hours, 12 hours to 20 hours, 14 hours to 18 hours, or 15 hours to 17 hours. In a more specific embodiment, the reaction in step (b) is allowed to proceed for 16 hours. In another embodiment, the reaction in step (b) is allowed to proceed for 14 hours to 30 hours, 18 hours to 26 hours, 20 hours to 24 hours or 19 hours to 23 hours. In a more specific embodiment, the reaction in step (b) is allowed to proceed for 22 hours.

The reaction in step (b) can be carried out at any suitable temperature. In one embodiment, the reaction can be carried out at a temperature from 10° C. to 50° C., from 10° C. to 40° C., or from 10° C. to 30° C. In another embodiment, the reaction can be carried out at a temperature from 15° C. to 25° C., from 16° C. to 24° C., from 17° C. to 23° C., from 18° C. to 22° C. or from 19° C. to 21° C. In yet another embodiment, the reaction can be carried out at 15° C., 16° C., 17° C., 18° C., 19° C., 20° C., 21° C., 22° C., 23° C., 24° C. or 25° C. Alternatively, the reaction can be carried out at a low temperature, such as less than 10° C. or less than 0° C. (provided that the solution is prevented from freezing, e.g., by the presence of an organic solvent used to dissolve the cytotoxic agent and/or the bifunctional crosslinking reagent). In one embodiment, the reaction can be carried out at a temperature from −10° C. to 0° C., from 0° C. to 10° C., or from 0° C. to 5° C.

In certain embodiments, the processes of the present invention further comprises a quenching step after step (b). In one embodiment, the quenching is achieved by rapidly adjusting the pH of the second mixture obtained from step (b) to a low pH (e.g., pH less than or equal to 6.5, less than or equal to 6.0, less than or equal to 5.5, less than or equal to 5.4, less than or equal to 5.3, less than or equal to 5.2, less than or equal to 5.1, less than or equal to 5.0). In one embodiment, the pH of the second mixture is adjusted to a pH of 4.0 to 6.5, 4.5 to 6.0, 4.5 to 5.5, 4.6 to 5.4, 4.7 to 5.3, 4.8 to 5.2 or 4.9 to 5.1. In a more specific embodiment, the pH of the second mixture is adjusted to pH 5.0. The pH of the second mixture can be adjusted by adding an acid to the second mixture. More specifically, the pH of the second mixture can be adjusted by adding acetic acid to the second mixture.

In another embodiment, quenching is achieved by adding one or more quenching agents to the second mixture to quench any unreacted cytotoxic agent and/or unreacted bifunctional crosslinking reagent. As used herein, the term "quenching agent" refers to a reagent that reacts with the free cytotoxic agent and/or bifunctional crosslinking reagent.

In one embodiment, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the cytotoxic agent is quenched. The quenching step can help prevent the dimerization of the cytotoxic agent, particular the cytotoxic agent having an unreacted thiol group (such as DM1). The dimerized cytotoxic agent can be difficult to remove. The quenching step may also minimize any unwanted thiol-disulfide interchange reaction with the native antibody disulfide groups. Upon quenching with polar, charged thiol-quenching reagents (such as 4-maleimidobutyric acid or 3-maleimidopropionic acid), the excess, unreacted cytotoxic agent is converted into a polar, charged, water-soluble adduct that can be easily separated from the covalently-linked conjugate during the purification step. Quenching with non-polar and neutral thiol-quenching reagents can also be used.

In one embodiment, the mixture is quenched by contacting the mixture with a quenching reagent that reacts with the unreacted bifunctional crosslinking reagent. For example, nucleophiles can be added to the mixture in order to quench any unreacted bifunctional crosslinking reagent. The nucleophile preferably is an amino group containing nucleophile, such as lysine, taurine and hydroxylamine.

In certain embodiments, the reaction of step (b) is allowed to proceed to completion before the quenching step, i.e., adjusting the pH and/or contacting the second mixture with a quenching agent described above.

Following the reaction step (b), the cell-binding agent cytotoxic agent conjugate is subjected to a purification step. In this regard, the cell-binding agent cytotoxic agent conjugate can be purified from the other components of the mixture (e.g., free bifunctional crosslinking agent, free cytotoxic agent and reaction by-products) using tangential flow filtration (TFF), which is a membrane-based tangential flow filtration process, non-adsorptive chromatography, adsorptive chromatography, adsorptive filtration, selective precipitation, or any other suitable purification process, as well as combinations thereof.

In one embodiment of the invention, the cell-binding agent cytotoxic agent conjugate is purified using a single purification step (e.g., TFF). Preferably, the conjugate is purified and exchanged into the appropriate formulation using a single purification step (e.g., TFF). In another embodiment of the invention, the cell-binding agent cytotoxic agent conjugate is purified using two sequential purification steps. For example, the conjugate can be first purified by selective precipitation, adsorptive filtration, absorptive chromatography or non-absorptive chromatography, followed by purification with TFF. One of ordinary skill in the art will appreciate that purification of the cell-binding agent cytotoxic agent conjugate enables the isolation of a stable conjugate comprising the cell-binding agent chemically coupled to the cytotoxic agent.

Any suitable TFF systems may be utilized for purification, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., Mab-Select, GE Healthcare, Piscataway, N.J.), where the cell-binding agent is an antibody, and lectin affinity resins, e.g. Lentil Lectin Sepharose resin (GE Healthcare, Piscataway, N.J.), where the cell-binding agent bears appropriate lectin binding sites. Alternatively an antibody specific to the cell-binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

The cell-binding agent-cytotoxic agent conjugates prepared by the processes of the present invention have substantially high purity and stability. In one aspect of the invention, a cell-binding agent-cytotoxic agent conjugate of substantially high purity has one or more of the following features: (a) less than 25%, less than 20%, less than 15% (e.g., less than or equal to 15%, 14%, 13%, 12%, 11%, 10%, 9%, 8%, 7%, 6%, 5%, 4%, 3%, 2% or 1%) of antibody fragmentation, (b) greater than 90% (e.g., greater than or equal to 91%, 92%, 93%, 94%, 95%, 96%, 97%, 98%, 99%, or 100%), preferably greater than 95%, of conjugate species are monomeric, (c) unconjugated linker level in the conjugate preparation is less than about 10% (e.g., less than or equal to about 9%, 8%, 7%, 6%, 5%, 4%, 3%, 2%, 1%, or 0%) (relative to total linker), (d) less than 10% of conjugate species are crosslinked (e.g., less than or equal to about 9%, 8%, 7%, 6%, 5%, 4%, 3%, 2%, 1%, or 0%), (e) free cytotoxic agent level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent) and/or (f) no substantial increase in the level of free cytotoxic agent upon storage (e.g., after about 1 week, about 2 weeks, about 3 weeks, about 1 month, about 2 months, about 3 months, about 4 months, about 5 months, about 6 months, about 1 year, about 2 years, about 3 years, about 4 years, or about 5 years). "Substantial increase" in the level of free cytotoxic agent means that after certain storage time (e.g., about 1 week, about 2 weeks, about 3 weeks, about 1 month, about 2 months, about 3 months, about 4 months, about 5 months, about 6 months, about 1 year, about 2 years, about 3 years, about 4 years, or about 5 years), the increase in the level of free cytotoxic agent is less than about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.2%, about 2.5%, about 2.7%, about 3.0%, about 3.2%, about 3.5%, about 3.7%, or about 4.0%.

As used herein, the term "unconjugated linker" refers to the cell-binding agent that is covalently linked with the bifunctional crosslinking reagent, wherein the cell-binding agent is not covalently coupled to the cytotoxic agent through the linker of the bifunctional crosslinking reagent (i.e., the "unconjugated linker" can be represented by CBA-L, wherein CBA represents the cell-binding agent and L represents the bifunctional crosslinking reagent. In contrast, the cell-binding agent cytotoxic agent conjugate can be represented by CBA-L-D, wherein D represents the cytotoxic agent).

In one embodiment, the average molar ratio of the cytotoxic agent to the cell-binding agent (i.e., DAR) in the cell-binding agent cytotoxic agent conjugate is about 1 to about 10, about 2 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

Cell-Binding Agent

For use in the processes of the present invention, the cell-binding agent can be any suitable agent that binds to a cell, typically and preferably an animal cell (e.g., a human cell). The cell-binding agent preferably is a peptide or a polypeptide. Suitable cell-binding agents include, for example, antibodies (e.g., monoclonal antibodies and fragments thereof), interferons (e.g. alpha., beta., gamma.), lymphokines (e.g., IL-2, IL-3, IL-4, IL-6), hormones (e.g., insulin, TRH (thyrotropin releasing hormone), MSH (melanocyte-stimulating hormone), steroid hormones, such as androgens and estrogens), growth factors and colony-stimulating factors such as EGF, TGF-alpha, FGF, VEGF, G-CSF, M-CSF and GM-CSF (Burgess, Immunology Today 5:155-158 (1984)), nutrient-transport molecules (e.g., transferrin), vitamins (e.g., folate) and any other agent or molecule that specifically binds a target molecule on the surface of a cell.

Where the cell-binding agent is an antibody, it binds to an antigen that is a polypeptide or a glycotope and may be a transmembrane molecule (e.g., receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-.beta.; platelet-derived growth factor (PDGF); fibroblast growth factor such as aFGF and bFGF; epidermal growth factor (EGF); transforming growth factor (TGF) such as TGF-alpha and TGF-beta, including TGF-.beta.1, TGF-.beta.2, TGF-.beta.3, TGF-.beta.4, or TGF-.beta.5; insulin-like growth factor-I and -II (IGF-I and IGF-II); des(1-3)-IGF-I (brain IGF-I); insulin-like growth factor binding proteins; EpCAM; GD3; FLT3; PSMA; PSCA; MUC1; MUC16; STEAP; CEA; TENB2; EphA receptors; EphB receptors; folate receptor; FOLR1; mesothelin; crypto; $\alpha_v\beta_6$; integrins; VEGF, VEGFR; EGFR; fibroblast growth factor receptor (FGFR) (e.g., FGFR1, FGFR2, FGFR3, FGFR4); transferrin receptor; IRTA1; IRTA2; IRTA3; IRTA4; IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in U.S. Patent Application Publication No. 2008/0171040 or U.S. Patent Application Publication No. 2008/0305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3, or HER4 receptor; endoglin; c-Met; IGF1R; prostate antigens such as PCA3, PSA, PSGR, NGEP, PSMA, PSCA, TMEFF2, and STEAP1; LGR5; B7H4; and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

The term "antibody," as used herein, refers to any immunoglobulin, any immunoglobulin fragment, such as Fab, Fab', F(ab').sub.2, dsFv, sFv, minibodies, diabodies, tribodies, tetrabodies (Parham, J. Immunol., 131: 2895-2902 (1983); Spring et al. J. Immunol., 113: 470-478 (1974); Nisonoff et al. Arch. Biochem. Biophys., 89: 230-244 (1960), Kim et al., Mol. Cancer Ther., 7: 2486-2497 (2008), Carter, Nature Revs., 6: 343-357 (2006)), or immunoglobulin chimera, which can bind to an antigen on the surface of a cell (e.g., which contains a complementarity determining region (CDR)). Any suitable antibody can be used as the cell-binding agent. One of ordinary skill in the art will appreciate that the selection of an appropriate antibody will depend upon the cell population to be targeted. In this regard, the type and number of cell surface molecules (i.e., antigens) that are selectively expressed in a particular cell population (typically and preferably a diseased cell population) will govern the selection of an appropriate antibody for use in the inventive composition. Cell surface expression profiles are known for a wide variety of cell types, including tumor cell types, or, if unknown, can be determined using routine molecular biology and histochemistry techniques.

The antibody can be polyclonal or monoclonal, but is most preferably a monoclonal antibody. As used herein, "polyclonal" antibodies refer to heterogeneous populations of antibody molecules, typically contained in the sera of immunized animals. "Monoclonal" antibodies refer to homogenous populations of antibody molecules that are specific to a particular antigen. Monoclonal antibodies are typically produced by a single clone of B lymphocytes ("B cells"). Monoclonal antibodies may be obtained using a variety of techniques known to those skilled in the art, including standard hybridoma technology (see, e.g., Kohler and Milstein, Eur. J. Immunol., 5: 511-519 (1976), Harlow and Lane (eds.), Antibodies: A Laboratory Manual, CSH Press (1988), and C. A. Janeway et al. (eds.), Immunobiology, 5.sup.th Ed., Garland Publishing, New York, N.Y. (2001)). In brief, the hybridoma method of producing monoclonal antibodies typically involves injecting any suitable animal, typically and preferably a mouse, with an antigen (i.e., an "immunogen"). The animal is subsequently sacrificed, and B cells isolated from its spleen are fused with human myeloma cells. A hybrid cell is produced (i.e., a "hybridoma"), which proliferates indefinitely and continuously secretes high titers of an antibody with the desired specificity in vitro. Any appropriate method known in the art can be used to identify hybridoma cells that produce an antibody with the desired specificity. Such methods include, for example, enzyme-linked immunosorbent assay (ELISA), Western blot analysis, and radioimmunoassay. The population of hybridomas is screened to isolate individual clones, each of which secretes a single antibody species to the antigen. Because each hybridoma is a clone derived from fusion with a single B cell, all the antibody molecules it produces are identical in structure, including their antigen binding site and isotype. Monoclonal antibodies also may be generated using other suitable techniques including EBV-hybridoma technology (see, e.g., Haskard and Archer, J. Immunol. Methods, 74(2): 361-67 (1984), and Roder et al., Methods Enzymol., 121: 140-67 (1986)), bacteriophage vector expression systems (see, e.g., Huse et al., Science, 246: 1275-81 (1989)), or phage display libraries comprising antibody fragments, such as Fab and scFv (single chain variable region) (see, e.g., U.S. Pat. Nos. 5,885,793 and 5,969,108, and International Patent Application Publications WO 92/01047 and WO 99/06587).

The monoclonal antibody can be isolated from or produced in any suitable animal, but is preferably produced in a mammal, more preferably a mouse or human, and most preferably a human. Methods for producing an antibody in mice are well known to those skilled in the art and are described herein. With respect to human antibodies, one of ordinary skill in the art will appreciate that polyclonal antibodies can be isolated from the sera of human subjects vaccinated or immunized with an appropriate antigen. Alternatively, human antibodies can be generated by adapting known techniques for producing human antibodies in non-human animals such as mice (see, e.g., U.S. Pat. Nos. 5,545,806, 5,569,825, and 5,714,352, and U.S. Patent Application Publication No. 2002/0197266 A1).

While being the ideal choice for therapeutic applications in humans, human antibodies, particularly human monoclonal antibodies, typically are more difficult to generate than mouse monoclonal antibodies. Mouse monoclonal antibodies, however, induce a rapid host antibody response when administered to humans, which can reduce the therapeutic or diagnostic potential of the antibody-cytotoxic agent conjugate. To circumvent these complications, a monoclonal antibody preferably is not recognized as "foreign" by the human immune system.

To this end, phage display can be used to generate the antibody. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3.sup.rd Edition, Cold Spring Harbor Laboratory Press, New York (2001)). Phages encoding a variable region with the desired specificity are selected for specific binding to the desired antigen, and a complete human antibody is reconstituted comprising the selected variable domain. Nucleic acid sequences encoding the reconstituted antibody are introduced into a suitable cell line, such as a myeloma cell used for hybridoma production, such that human antibodies having the characteristics of monoclonal antibodies are secreted by the cell (see, e.g., Janeway et al., supra, Huse et al., supra, and U.S. Pat. No. 6,265,150). Alternatively, monoclonal antibodies can be generated from mice that are transgenic for specific human heavy and light chain immunoglobulin genes. Such methods are known in the art and described in, for example, U.S. Pat. Nos. 5,545,806 and 5,569,825, and Janeway et al., supra.

Most preferably the antibody is a humanized antibody. As used herein, a "humanized" antibody is one in which the complementarity-determining regions (CDR) of a mouse monoclonal antibody, which form the antigen binding loops of the antibody, are grafted onto the framework of a human antibody molecule. Owing to the similarity of the frameworks of mouse and human antibodies, it is generally accepted in the art that this approach produces a monoclonal antibody that is antigenically identical to a human antibody but binds the same antigen as the mouse monoclonal antibody from which the CDR sequences were derived. Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235: 959-973 (1994). While the antibody employed in the conjugate of the inventive composition most preferably is a humanized monoclonal antibody, a human monoclonal antibody and a mouse monoclonal antibody, as described above, are also within the scope of the invention.

Antibody fragments that have at least one antigen binding site, and thus recognize and bind to at least one antigen or receptor present on the surface of a target cell, also are within the scope of the invention. In this respect, proteolytic cleavage of an intact antibody molecule can produce a variety of antibody fragments that retain the ability to recognize and bind antigens. For example, limited digestion of an antibody molecule with the protease papain typically produces three fragments, two of which are identical and are referred to as the Fab fragments, as they retain the antigen binding activity of the parent antibody molecule. Cleavage of an antibody molecule with the enzyme pepsin normally produces two antibody fragments, one of which retains both antigen-binding arms of the antibody molecule, and is thus referred to as the F(ab').sub.2 fragment. Reduction of a F(ab').sub.2 fragment with dithiothreitol or mercaptoethylamine produces a fragment referred to as a Fab' fragment. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7: 697-704 (1994)). Antibody fragments in the context of the invention, however, are not limited to these exemplary types of antibody fragments. Any suitable antibody fragment that recognizes and binds to a desired cell surface receptor or antigen can be employed. Antibody fragments are further described in, for example, Parham, J. Immunol., 131: 2895-2902 (1983), Spring et al., J. Immunol., 113: 470-478 (1974), and Nisonoff et al., Arch. Biochem. Biophys., 89: 230-244 (1960). Antibody-antigen binding can be assayed using any suitable method known in the art, such as, for example, radioimmunoassay (RIA), ELISA, Western blot, immunoprecipitation, and competitive inhibition assays (see, e.g., Janeway et al., supra, and U.S. Patent Application Publication No. 2002/0197266 A1).

In addition, the antibody can be a chimeric antibody or an antigen binding fragment thereof. By "chimeric" it is meant that the antibody comprises at least two immunoglobulins, or fragments thereof, obtained or derived from at least two different species (e.g., two different immunoglobulins, such as a human immunoglobulin constant region combined with a murine immunoglobulin variable region). The antibody also can be a domain antibody (dAb) or an antigen binding fragment thereof, such as, for example, a camelid antibody (see, e.g., Desmyter et al., Nature Struct. Biol., 3: 752, (1996)), or a shark antibody, such as, for example, a new antigen receptor (IgNAR) (see, e.g., Greenberg et al., Nature, 374: 168 (1995), and Stanfield et al., Science, 305: 1770-1773 (2004)).

Any suitable antibody can be used in the context of the invention. For example, the monoclonal antibody J5 is a murine IgG2a antibody that is specific for Common Acute Lymphoblastic Leukemia Antigen (CALLA) (Ritz et al., Nature, 283: 583-585 (1980)), and can be used to target cells that express CALLA (e.g., acute lymphoblastic leukemia cells). The monoclonal antibody MY9 is a murine IgG1 antibody that binds specifically to the CD33 antigen (Griffin et al., Leukemia Res., 8: 521 (1984)), and can be used to target cells that express CD33 (e.g., acute myelogenous leukemia (AML) cells).

Similarly, the monoclonal antibody anti-B4 (also referred to as B4) is a murine IgG1 antibody that binds to the CD19 antigen on B cells (Nadler et al., J. Immunol., 131: 244-250 (1983)), and can be used to target B cells or diseased cells that express CD19 (e.g., non-Hodgkin's lymphoma cells and chronic lymphoblastic leukemia cells). N901 is a murine monoclonal antibody that binds to the CD56 (neural cell adhesion molecule) antigen found on cells of neuroendocrine origin, including small cell lung tumor, which can be used in the conjugate to target drugs to cells of neuroendocrine origin. The J5, MY9, and B4 antibodies preferably are resurfaced or humanized prior to their use as part of the conjugate. Resurfacing or humanization of antibodies is described in, for example, Roguska et al., Proc. Natl. Acad. Sci. USA, 91: 969-73 (1994).

In addition, the monoclonal antibody C242 binds to the CanAg antigen (see, e.g., U.S. Pat. No. 5,552,293), and can be used to target the conjugate to CanAg expressing tumors, such as colorectal, pancreatic, non-small cell lung, and gastric cancers. HuC242 is a humanized form of the monoclonal antibody C242 (see, e.g., U.S. Pat. No. 5,552,293). The hybridoma from which HuC242 is produced is deposited with ECACC identification Number 90012601. HuC242 can be prepared using CDR-grafting methodology (see, e.g., U.S. Pat. Nos. 5,585,089, 5,693,761, and 5,693,762) or resurfacing technology (see, e.g., U.S. Pat. No. 5,639,641). HuC242 can be used to target the conjugate to tumor cells expressing the CanAg antigen, such as, for example, colorectal, pancreatic, non-small cell lung, and gastric cancer cells.

To target ovarian cancer and prostate cancer cells, an anti-MUC1 antibody can be used as the cell-binding agent in the conjugate. Anti-MUC1 antibodies include, for example, anti-HMFG-2 (see, e.g., Taylor-Papadimitriou et al., Int. J. Cancer, 28: 17-21 (1981)), hCTMO1 (see, e.g., van H of et al., Cancer Res., 56: 5179-5185 (1996)), and DS6. Prostate cancer cells also can be targeted with the conjugate by using an anti-prostate-specific membrane antigen (PSMA) as the cell-binding agent, such as J591 (see, e.g., Liu et al., Cancer Res., 57: 3629-3634 (1997)). Moreover, cancer cells that express the Her2 antigen, such as breast, prostate, and ovarian cancers, can be targeted with the conjugate by using anti-Her2 antibodies, e.g., trastuzumab, as the cell-binding agent. Cells that express epidermal growth factor receptor (EGFR) and variants thereof, such as the type III deletion mutant, EGFRvIII, can be targeted with the conjugate by using anti-EGFR antibodies. Anti-EGFR antibodies are described in International Patent Application Nos. PCT/US11/058,385 and PCT/US11/058,378. Anti-EGFRvIII antibodies are described in U.S. Pat. Nos. 7,736,644 and 7,628,986 and U.S. Application Publications 2010/0111979, 2009/0240038, 2009/0175887, 2009/0156790, and 2009/0155282. Anti-IGF-IR antibodies that bind to insulin-like growth factor receptor, such as those described in U.S. Pat. No. 7,982,024, also can be used in the conjugate. Antibodies that bind to CD27L, Cripto, CD138, CD38, EphA2, integrins, CD37, folate, CD20, PSGR, NGEP, PSCA, TMEFF2, STEAP1, endoglin, and Her3 also can be used in the conjugate.

In one embodiment, the antibody is selected from the group consisting of huN901, huMy9-6, huB4, huC242, an anti-HER2 antibody (e.g., trastuzumab), bivatuzumab, sibrotuzumab, rituximab, huDS6, anti-mesothelin antibodies described in International Patent Application Publication WO 2010/124797 (such as MF-T), anti-cripto antibodies described in U.S. Patent Application Publication 2010/0093980 (such as huB3F6), anti-CD138 antibodies described in U.S. Patent Application Publication 2007/0183971 (such as huB-B4), anti-EGFR antibodies described in International Patent Application Nos. PCT/US11/058,385 and PCT/US11/058,378 (such as EGFR-7), anti-EGFRvIII antibodies described U.S. Pat. Nos. 7,736,644 and 7,628,986 and U.S. Patent Application Publications 2010/0111979, 2009/0240038, 2009/0175887, 2009/0156790 and 2009/0155282, humanized EphA2 antibodies described in International Patent Application Publications WO 2011/039721 and WO 2011/039724 (such as 2H11R35R74); anti-CD38 antibodies described in International Patent Application Publication WO 2008/047242 (such as hu38SB19), antifolate antibodies described in International Patent Application Publication WO 2011/106528, and U.S. Patent Application Publication 2012/0009181 (e.g., huMov19); anti-IGF1R antibodies described in U.S. Pat. Nos. 5,958,872, 6,596,743, and 7,982,024; anti-CD37 antibodies described in U.S. Patent Application Publication 2011/0256153 (e.g., huCD37-3); anti-integrin $\alpha_v\beta_6$ antibodies described in U.S. Application Publication 2006/0127407 (e.g., CNTO95); and anti-Her3 antibodies described in International Patent Application Publication WO 2012/019024. In one embodiment, the cell-binding agent is an antibody or an antigen binding fragment thereof that binds to FGFR2 (e.g., those described in US2014/030820, the entire teachings of which is incorporated herein by reference). In another embodiment, the cell-binding agent is an antibody or an antigen binding fragment thereof that binds to FGFR2 and FGFR4 (e.g., those described in US 2014/301946, the entire teachings of which is incorporated herein by reference).

In yet another embodiment, the cell-binding agent binds to human FGFR3 (SEQ ID NO: 11). More specifically, the cell-binding agent binds to human FGFR3 (SEQ ID NO 11) and comprises a CDRH1 having the sequence GYMFTSYGIS (SEQ ID NO 1), a CDRH2 having the sequence WVSTYNGDTNYAQKFQG (SEQ ID NO 2), a CDRH3 having the sequence VLGYYDSIDGYYYGMDV (SEQ ID NO 3), a CDRL1 having the sequence GGNNIGDKSVH (SEQ ID NO 4), a CDRL2 having the sequence LDTERPS (SEQ ID NO 5), and a CDRL3 having the sequence QVWDSGSDHVV (SEQ ID NO 6). Even more specifically, the cell binding agent further comprises a variable heavy amino acid sequence of:

```
                                           (SEQ ID NO 7)
EVQLVQSGAEVKKPGASVKVSCKASGYMFTSYGISWVRQAPGQGLEWMGW

VSTYNGDTNYAQKFQGRVTVTTDTSTSTAYMELRSLRSEDTAVYYCARVL

GYYDSIDGYYYGMDVWGQGTTVTVSS
``` and a variable light amino acid sequence of:

```
                                           (SEQ ID NO 8)
QSVLTQPPSLSVAPGKTATFTCGGNNIGDKSVHWYRQKPGQAPVLVMYLD

TERPSGIPERMSGSNFGNTATLTITRVEAGDEADYYCQVWDSGSDHVVFG

GGTKLTVLG.
```

In another more specific embodiment, the cell-binding agent further comprises a light chain comprising the amino acid sequence of SEQ ID NO: 10 and a heavy chain comprising the amino acid sequence of SEQ ID NO: 9. In another embodiment, the cell-binding agent further comprises two light chains each comprising the amino acid sequence of SEQ ID NO: 10 and two heavy chains each comprising the amino acid sequence of SEQ ID NO: 9.

Particularly preferred antibodies are humanized monoclonal antibodies described herein. Examples include, but are not limited to, huN901, huMy9-6, huB4, huC242, a humanized monoclonal anti-Her2 antibody (e.g., trastuzumab), bivatuzumab, sibrotuzumab, CNTO95, huDS6, and rituximab (see, e.g., U.S. Pat. Nos. 5,639,641 and 5,665,357, U.S. Provisional Patent Application No. 60/424,332 (which is related to U.S. Pat. No. 7,557,189), International (PCT) Patent Application Publication WO 02/16401, Pedersen et al., supra, Roguska et al., supra, Liu et al., supra, Nadler et al., supra, Colomer et al., Cancer Invest., 19: 49-56 (2001), Heider et al., Eur. J. Cancer, 31A: 2385-2391 (1995), Welt et al., J. Clin. Oncol., 12: 1193-1203 (1994), and Maloney et al., Blood, 90: 2188-2195 (1997)). Other humanized monoclonal antibodies are known in the art and can be used in connection with the invention.

In one embodiment, the cell-binding agent is huMy9-6, or other related antibodies, which are described in U.S. Pat. Nos. 7,342,110 and 7,557,189 (incorporated herein by reference).

In another embodiment, the cell-binding agent is an anti-folate receptor antibody described in U.S. Provisional Application Nos. 61/307,797, 61/346,595, 61/413,172 and U.S. application Ser. No. 13/033,723 (published as US 2012-0009181 A1). The teachings of all these applications are incorporated herein by reference in its entirety.

In another embodiment, the cell-binding agent is an humanized anti-folate antibody or antigen binding fragment thereof that specifically binds a human folate receptor 1 (FOLR1), wherein the antibody comprises: (a) a heavy chain CDR1 comprising GYFMN; a heavy chain CDR2 comprising RIHPYDGDTFYNQXaa$_1$FXaa$_2$Xaa$_3$; and a heavy chain CDR3 comprising YDGSRAMDY; and (b) a light chain CDR1 comprising KASQSVSFAGTSLMH; a light chain CDR2 comprising RASNLEA; and a light chain CDR3 comprising QQSREYPYT; wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG.

In another embodiment, the anti-folate antibody is a humanized antibody or antigen binding fragment thereof that specifically binds the human folate receptor 1 comprising the heavy chain having the amino acid sequence of

QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK.

In another embodiment, the anti-folate antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate antibody is a humanized antibody or antigen binding fragment thereof comprising a heavy chain variable domain at least about 90%, 95%, 99% or 100% identical to QVQLVQSGAEVVKPGASVKISCKASGYTFTGYFMN-WVKQSPGQSLEWIGRIHPYDG DTFYNQKFQG-KATLTVDKSSNTAHMELLSLTSEDFAVYYCTRYDGS RAMDYWGQG TTVTVSS, and a light chain variable domain at least about 90%, 95%, 99% or 100% identical to

DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKR;

or

DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKR.

While the cell-binding agent preferably is an antibody, the cell-binding agent also can be a non-antibody molecule. Suitable non-antibody molecules include, for example, interferons (e.g., alpha, beta, or gamma interferon), lymphokines (e.g., interleukin 2 (IL-2), IL-3, IL-4, or IL-6), hormones (e.g., insulin), growth factors (e.g., EGF, TGF-alpha, FGF, and VEGF), colony-stimulating factors (e.g., G-CSF, M-CSF, and GM-CSF (see, e.g., Burgess, Immunology Today, 5: 155-158 (1984)), somatostatin, and transferrin (see, e.g., O'Keefe et al., J. Biol. Chem., 260: 932-937 (1985)). For example, GM-CSF, which binds to myeloid cells, can be used as a cell-binding agent to target acute myelogenous leukemia cells. In addition, IL-2, which binds to activated T-cells, can be used for prevention of transplant graft rejection, for therapy and prevention of graft-versus-host disease, and for treatment of acute T-cell leukemia. Epidermal growth factor (EGF) can be used to target squamous cancers such as lung cancer and head and neck cancer. Somatostatin can be used to target neuroblastoma cells and other tumor cell types Cytotoxic Agent A "cytotoxic agent," as used herein, refers to any compound that results in the death of a cell, induces cell death, or decreases cell viability. Suitable cytotoxic agents include, for example, maytansinoids and conjugatable ansamitocins (see, for example, International Patent Application No. PCT/US11/59131, filed Nov. 3, 2011), taxoids, CC-1065 and CC-1065 analogs, and dolastatin and dolastatin analogs. In a specific embodiment of the invention, the cytotoxic agent is a maytansinoid, including maytansinol and maytansinol analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

Examples of maytansinol analogs having a modified aromatic ring include: (1) C-19-dechloro (U.S. Pat. No. 4,256,746) (prepared by LAH reduction of ansamytocin P2), (2) C-20-hydroxy (or C-20-demethyl)+/−C-19-dechloro (U.S. Pat. Nos. 4,361,650 and 4,307,016) (prepared by demethylation using *Streptomyces* or Actinomyces or dechlorination using LAH), and (3) C-20-demethoxy, C-20-acyloxy (—OCOR), +/−dechloro (U.S. Pat. No. 4,294,757) (prepared by acylation using acyl chlorides).

Examples of maytansinol analogs having modifications of positions other than an aromatic ring include: (1) C-9-SH (U.S. Pat. No. 4,424,219) (prepared by the reaction of maytansinol with H.sub.2S or P.sub.2S.sub.5), (2) C-14-alkoxymethyl (demethoxy/CH.sub.2OR) (U.S. Pat. No. 4,331,598), (3) C-14-hydroxymethyl or acyloxymethyl (CH.sub.2OH or CH.sub.2OAc) (U.S. Pat. No. 4,450,254)

(prepared from Nocardia), (4) C-15-hydroxy/acyloxy (U.S. Pat. No. 4,364,866) (prepared by the conversion of maytansinol by *Streptomyces*), (5) C-15-methoxy (U.S. Pat. Nos. 4,313,946 and 4,315,929) (isolated from *Trewia nudiflora*), (6) C-18-N-demethyl (U.S. Pat. Nos. 4,362,663 and 4,322,348) (prepared by the demethylation of maytansinol by *Streptomyces*), and (7) 4,5-deoxy (U.S. Pat. No. 4,371,533) (prepared by the titanium trichloride/LAH reduction of maytansinol).

In a specific embodiment of the invention, the cytotoxic agent can be used in the processes of the present invention is the thiol-containing maytansinoid DM1, also known as $N^{2'}$-deacetyl-$N^{2'}$-(3-mercapto-1-oxopropyl)-maytansine. The structure of DM1 is represented by formula (I):

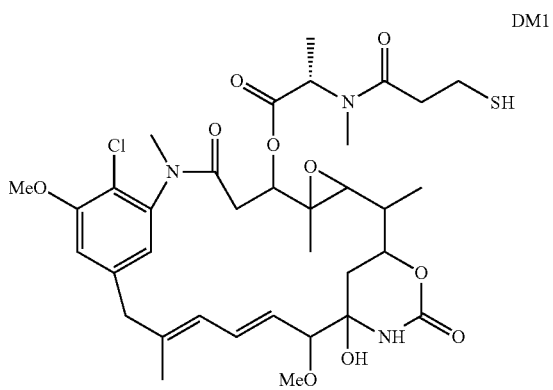 [SMILES: COc1cc2cc(c1Cl)N(C)C(=O)CC(OC(=O)[C@H](C)N(C)C(=O)CCS)C1(C)OC1C(C)C1CC(O)(NC(=O)O1)C(OC)/C=C/C=C(\C)C2]

DM1

In another preferred embodiment of the invention, t the cytotoxic agent can be used in the processes of the present invention is the thiol-containing maytansinoid DM1, also known as $N^{2'}$-deacetyl-$N^{2'}$-(4-methyl-4-mercapto-1-oxopentyl)-maytansine. The structure of DM4 is represented by formula (II):

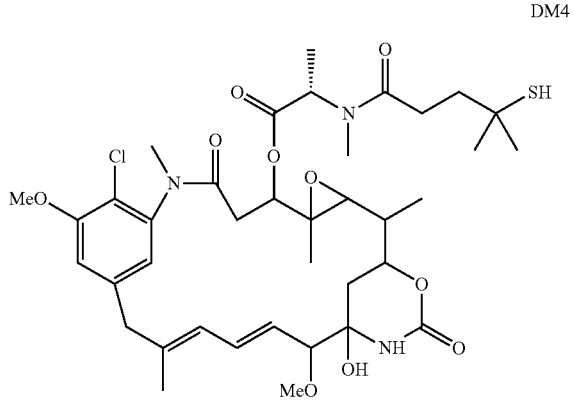 [SMILES: COc1cc2cc(c1Cl)N(C)C(=O)CC(OC(=O)[C@H](C)N(C)C(=O)CCC(C)(C)S)C1(C)OC1C(C)C1CC(O)(NC(=O)O1)C(OC)/C=C/C=C(\C)C2]

DM4

Other maytansinoids may be used in the context of the invention, including, for example, thiol and disulfide-containing maytansinoids bearing a mono or di-alkyl substitution on the carbon atom bearing the sulfur atom. Particularly preferred is a maytansinoid having at the C-3 position (a) C-14 hydroxymethyl, C-15 hydroxy, or C-20 desmethyl functionality, and (b) an acylated amino acid side chain with an acyl group bearing a hindered sulfhydryl group, wherein the carbon atom of the acyl group bearing the thiol functionality has one or two substituents, said substituents being a linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Additional maytansinoids for use in the context of the invention include compounds represented by formula (III):

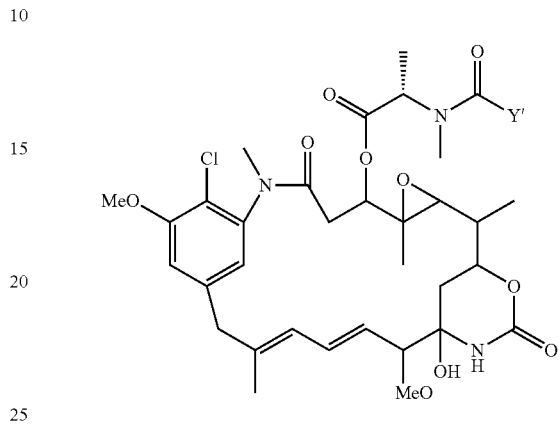

wherein Y' represents $(CR_7R_8)_l(CR_9=CR_{10})_p(C\equiv C)_qA_o(CR_5R_6)_mD_u(CR_{11}=CR_{12})_r(C\equiv C)_sB_l(CR_3R_4)_nCR_1R_2SZ$, wherein $R_1$ and $R_2$ are each independently a linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein A, B, D are cycloalkyl or cycloalkenyl having 3-10 carbon atoms, simple or substituted aryl, or heterocyclic aromatic, or heterocycloalkyl radical, wherein $R_3$, $R_4$, $R_5$, $R_6$, $R_7$, $R_8$, $R_9$, $R_{10}$, $R_{11}$, and $R_{12}$ are each independently H, a linear alkyl or alkenyl having from 1 to 10 carbon atoms, branched or cyclic alkyl or alkenyl having from 3 to 10 carbon atoms, phenyl, substituted phenyl or heterocyclic aromatic, or heterocycloalkyl radical, wherein l, m, n, o, p, q, r, s, and t are each independently zero or an integer from 1 to 5, provided that at least two of l, m, n, o, p, q, r, s and t are not zero at any one time, and wherein Z is H, SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic, or heterocycloalkyl radical. Preferred embodiments of formula (III) include compounds of formula (III) wherein (a) $R_1$ is H, $R_2$ is methyl and Z is H, (b) $R_1$ and $R_2$ are methyl and Z is H, (c) $R_1$ is H, $R_2$ is methyl, and Z is —$SCH_3$, and (d) $R_1$ and $R_2$ are methyl, and Z is —$SCH_3$.

Such additional maytansinoids also include compounds represented by formula (IV-L), (IV-D), or (IV-D,L):

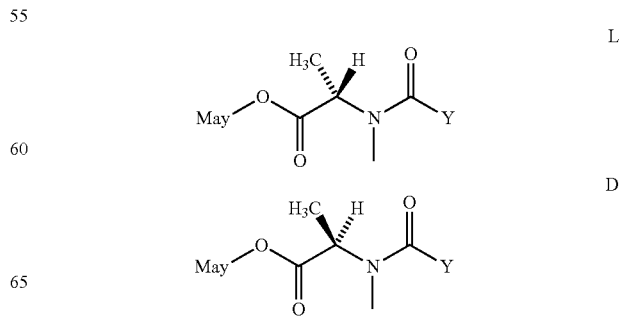

L

D

-continued

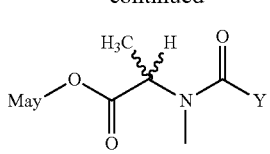

L,D wherein Y represents $(CR_7R_8)_l(CR_5R_6)_m(CR_3R_4)_n CR_1R_2SZ$, wherein $R_1$ and $R_2$ are each independently linear alkyl, or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, and wherein $R_2$ also can be H, wherein $R_3$, $R_4$, $R_5$, $R_6$, $R_7$, and $R_8$ are each independently H, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, wherein Z is H, SR, or COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocycloalkyl radical, and wherein May represents a maytansinoid which bears the side chain at C-3, C-14 hydroxymethyl, C-15 hydroxy, or C-20 desmethyl. Preferred embodiments of formulas (IV-L), (IV-D) and (IV-D,L) include compounds of formulas (IV-L), (IV-D) and (IV-D,L) wherein (a) $R_1$ is H, $R_2$ is methyl, $R_5$, $R_6$, $R_7$, $R_8$ are each H, l and m are each 1, n is 0, and Z is H, (b) $R_1$ is H, $R_2$ is methyl, $R_5$, $R_6$, $R_7$, $R_8$ are each H, l and m are 1, n is 0, and Z is H, (c) $R_1$ is H, $R_2$ is methyl, $R_5$, $R_6$, $R_7$, $R_8$ are each H, l and m are each 1, n is 0, and Z is —$SCH_3$, or (d) $R_1$ and $R_2$ are methyl, $R_5$, $R_6$, $R_7$, $R_8$ are each H, l and m are 1, n is 0, and Z is —$SCH_3$. Preferably the cytotoxic agent is represented by formula (IV-L).

Additional preferred maytansinoids also include compounds represented by formula (V):

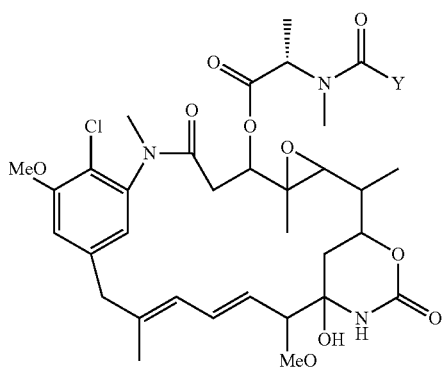

wherein $(CR_7R_8)_l(CR_5R_6)_m(CR_3R_4)_n CR_1R_2SZ$, wherein $R_1$ and $R_2$ are each independently linear alkyl, or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, and wherein $R_2$ also can be H, wherein $R_3$, $R_4$, $R_5$, $R_6$, $R_7$, and $R_8$ are each independently H, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, wherein Z is H, SR, or COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocycloalkyl radical, and wherein May represents a maytansinoid which bears the side chain at C-3, C-14 hydroxymethyl, C-15 hydroxy, or C-20 desmethyl. Preferred embodiments of formulas (IV-L), (IV-D) and (IV-D,L) include compounds of formulas (IV-L), (IV-D) and (IV-D,L) wherein (a) $R_1$ is H, $R_2$ is methyl, $R_5$, $R_6$, $R_7$, $R_8$ are each H, l and m are each 1, n is 0, and Z is H, (b) $R_1$ is H, $R_2$ is methyl, $R_5$, $R_6$, $R_7$, $R_8$ are each H, l and m are 1, n is 0, and Z is H, (c) $R_1$ is H, $R_2$ is methyl, $R_5$, $R_6$, $R_7$, $R_8$ are each H, l and m are each 1, n is 0, and Z is —$SCH_3$, or (d) $R_1$ and $R_2$ are methyl, $R_5$, $R_6$, $R_7$, $R_8$ are each H, l and m are 1, n is 0, and Z is —SCH.sub.3.

Preferred embodiments of formula (V) include compounds of formula (V) wherein (a) $R_1$ is H, $R_2$ is methyl, $R_5$, $R_6$, $R_7$, and $R_8$ are each H; l and m are each 1; n is 0; and Z is H, (b) $R_1$ and $R_2$ are methyl; $R_5$, $R_6$, $R_7$, and $R_8$ are each H, l and m are 1; n is 0; and Z is H, (c) $R_1$ is H, $R_2$ is methyl, $R_5$, $R_6$, $R_7$, and $R_8$ are each H, l and m are each 1, n is 0, and Z is —$SCH_3$, or (d) $R_1$ and $R_2$ are methyl; $R_5$, $R_6$, $R_7$, and $R_8$ are each H, l and m are 1, n is 0, and Z is —$SCH_3$.

In addition to maytansinoids, the cytotoxic agent used in the conjugate can be a taxane or derivative thereof. Taxanes are a family of compounds that includes paclitaxel (Taxol®), a cytotoxic natural product, and docetaxel (Taxotere®), a semi-synthetic derivative, which are both widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell-binding agents.

In order that the invention described herein may be more fully understood, the following examples are set forth. It should be understood that these examples are for illustrative purposes only and are not to be construed as limiting this invention in any manner.

EXAMPLES

Example 1

Analytical Methods:

Antibody and conjugate concentrations were measured using experimentally determined or calculated extinction coefficients for the antibody and DM4 components at 252 nm and 280 nm.

Monomer, high molecular weight species were determined by SEC-HPLC, using a Tosoh Bioscience TSK G3000SWXL (7.8×300 mm), 5 um particle size column. The mobile phase was 160 mM Potassium Phosphate, 212 mM Potassium Chloride pH 7.0 containing 15% Isopropanol, run at a flow rate of 0.5 mL/minute, with detection by absorbance at 280 nm.

Antibody fragments were measured using an Agilent 2100 Bioanalyzer with 2100 Expert Software, using a Protein 230 kit (Part#5087-1518). Denatured samples are prepared by addition of denaturation buffer, supplemented to contain 1.6 mM N-ethylmaleimide (NEM), and samples are heated to 70° C. for 5 minutes. All other steps, including dilutions, sample and ladder loading and analysis is performed according to the Agilent Protein 230 kit instructions. Antibody fragmentation percentages are calculated by the sum of all peaks that are smaller than the antibody monomer species (excluding known glycosylation artifacts) divided by the sum of all antibody related peaks.

In Situ Reaction Preparation (Step (a) of the Present Processes)

In situ reactions for the formation of cytotoxic agent-linker compounds were carried out by reacting DM4 (12 mM) with SPDB or sulfo-SPDB linker (10 mM) in 70.0% (v/v) DMA, and 30% (v/v) of one of four study buffers (200 mM Succinate, pH 5.0; 20 mM Succinate, pH 5.0; 167 mM EPPS, 67 mM NaCl, 2 mM EDTA pH 8.2; 20 mM EPPS, pH 8.2). The mixtures were vortexed and incubated at 20.0° C. for 6 hours and used immediately without any purification.

Conjugate Preparation (Step (b) of the Present Processes):

Conjugation mixtures were prepared by mixing the appropriate quantity of conjugation buffer (50 mM EPPS, 20 mM sodium chloride, 2 mM EDTA, pH 8.2) with the calculated amount of DMA to reach a final DMA level of 2.5% or 10%. Antibody1, an anti-FOLR1 antibody, which had been previously buffer exchanged into conjugation buffer by gel filtration chromatography, was then added to this mixture to achieve the final target antibody concentration. The calculated amount of in situ reaction mixture required to achieve a maytansinoid-to-antibody ratio (MAR) of 3-to-4, was added and the reactions mixed immediately. The conjugation reactions were then incubated at 20.0° C. for 22 hours with mixing on an orbital shaker at 160 rpm. At the end of the incubation period, pH 8.2 reaction mixtures were pH adjusted by addition of 6.5% (v/v) of 1M acetic acid, and filtered through a 0.22 um PVDF filter. Filtered, pH adjusted reaction mixtures were purified by gel filtration, and the purified conjugates were analyzed by UV-Visible absorbance spectroscopy, size exclusion chromatography by high performance liquid chromatography (SEC-HPLC), and non-reduced CE-SDS (GelChip).

TABLE 1

| In Situ Condition | Conjugation Condition | Fragment (%) sSPDB | Fragment (%) SPDB | Monomer (%) sSPDB | Monomer (%) SPDB | Yield (%) sSPDB | Yield (%) SPDB | Maytansinoid Inc Efficiency (%) sSPDB | Maytansinoid Inc Efficiency (%) SPDB |
|---|---|---|---|---|---|---|---|---|---|
| 167 mM EPPS, pH 8.2 | 40 g/L 10% DMA | 11.2 | 11.3 | 95.8 | 95.3 | 87.4 | 89.5 | 87.1 | 78.2 |
| | 10 g/L 10% DMA | 9.5 | 9.4 | 96.3 | 95.7 | 90.9 | 89.0 | 66.9 | 74.7 |
| | 10 g/L 2.5% DMA | 13.4 | 11.9 | 96.7 | 96.1 | 90.3 | 86.7 | 67.1 | 60.1 |
| 20 mM EPPS, pH 8.2 | 40 g/L 10% DMA | 15.2 | 11.1 | 95.3 | 95.0 | 86.8 | 88.6 | 88.4 | 82.1 |
| | 10 g/L 10% DMA | 13.7 | 9.3 | 96.0 | 95.5 | 90.5 | 88.5 | 67.8 | 79.4 |
| | 10 g/L 2.5% DMA | n/d | n/d | n/d | n/d | n/d | n/d | n/d | n/d |

TABLE 2

| In Situ Condition | Conjugation Condition | Fragment (%) sSPDB | Fragment (%) SPDB | Monomer (%) sSPDB | Monomer (%) SPDB | Yield (%) sSPDB | Yield (%) SPDB | Inc Efficiency (rMAR/MAR, %) sSPDB | Inc Efficiency (rMAR/MAR, %) SPDB |
|---|---|---|---|---|---|---|---|---|---|
| 200 mM Succinate, pH 5.0 | 40 g/L 10% DMA (26/25) | n/d | n/d | n/d | n/d | n/d | n/d | n/d | n/d |
| | 10 g/L 10% DMA (10/09) | 9.1 | 9.7 | 96.26 | 95.74 | 91.0 | 89.3 | 66.1 | 68.6 |
| | 10 g/L 2.5% DMA | n/d | n/d | n/d | n/d | n/d | n/d | n/d | n/d |
| 10 mM Succinate, pH 5.0 | 40 g/L 10% DMA | n/d | n/d | n/d | n/d | n/d | n/d | n/d | n/d |
| | 10 g/L 10% DMA (14/13) | 12.1 | 10.4 | 96.05 | 95.42 | 89.4 | 87.8 | 67.1 | 80.4 |
| | 10 g/L 2.5% DMA | n/d | n/d | n/d | n/d | n/d | n/d | n/d | n/d |

As shown in Tables 1 and 2, when a buffer solution having high buffer capacity is used for the in situ reaction of sSPDB and DM4 (i.e., reaction of step (a)), the resulting conjugate has significantly less antibody fragmentation as compared to conjugates prepared by using a buffer with low buffer capacity. In contrast, the buffer capacity has no significant effect on antibody fragmentation when SPDB is used as the bifunctional crosslinking reagent. The structure for SPDB linker is shown below:

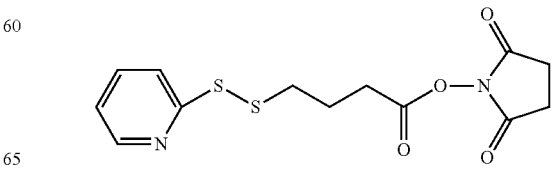

Example 2

Antibody2, an anti-FGFR3 antibody having a light chain with amino acid sequence of SEQ ID No: 10 and a heavy chain with amino acid sequence of SEQ ID NO: 9, was concentrated to 30 mg/mL and diafiltered into reaction buffer (50 mM EPPS, 20 mM sodium chloride, 2 mM EDTA, pH 8.2) for 10 diavolumes, and further concentrated to 45 g/L. A 1.2 molar ratio of DM4 (12 mM) relative to sulfo-SPDB (10 mM) was reacted with a 4.68 molar ratio of sulfo-SPDB relative to antibody in 167 mM EPPS, 66.7 mM NaCl, 2 mM EDTA, pH 8.2 and 70.0% (v/v) DMA. The in-situ reaction was carried out for 10±4 hours at 20±3° C., then added to Antibody2 with DMA to achieve a final Ab concentration of 20 mg/mL in 50 mM EPPS, 20 mM NaCl, 2 mM EDTA, pH 8.2±0.2 and 5.0% DMA (v/v). The conjugation reaction was carried out at 20.0±3.0° C. for 16±8 hours. After reaction, the conjugation mixture was rapidly pH adjusted to 5.0 by addition of 6.5% (v/v) of 1M acetic acid. The pH adjusted mixture is concentrated to 20 mg/mL, and diafiltered against basal formulation buffer (10 mM Acetate, pH 5.0±0.1) for 16 diavolumes. The purified conjugate was formulated at 5.0 mg/mL in 10 mM Acetate, 9% (w/v) Sucrose, 0.01% (w/v) Polysorbate-20 (Tween-20), pH 5.0, using concentrated stock solutions of sucrose (45%, w/v) and polysorbate-20 (10%, w/v).

I claim:

1. A process for preparing a cell-binding agent cytotoxic agent conjugate comprising the steps of:
   (a) reacting a cytotoxic agent with a bifunctional crosslinking reagent represented by the following structural formula:

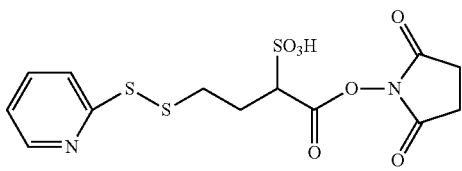 [SMILES: O=C(ON1C(=O)CCC1=O)C(CCSSc1ccccn1)S(=O)(=O)O]

or a salt thereof, in a buffer solution comprising a buffering agent to provide a first mixture comprising a cytotoxic agent-linker compound, wherein the buffer solution has high buffer capacity and the molar ratio of the buffering agent to the bifunctional crosslinking reagent is 2:1 to 8:1;
   (b) reacting the cytotoxic agent-linker compound in the first mixture obtained from step (a) with a cell-binding agent in a solution having a pH of 4 to 9 to provide a second mixture comprising the cell-binding agent cytotoxic agent conjugate,
   wherein the cell-binding agent is an antibody.

2. The process of claim 1, wherein the cell-binding agent is prone to fragmentation.

3. The process of claim 1, wherein the cytotoxic agent is a maytansinoid.

4. The process of claim 3, wherein the cytotoxic agent is DM4.

5. The process of claim 1, wherein molar ratio of the buffering agent to the bifunctional crosslinking reagent is 4:1 to 6:1.

6. The process of claim 5, wherein the molar ratio of the buffering agent to the bifunctional crosslinking reagent is 5:1.

7. The process of claim 1, wherein the buffer solution has a pH of 4 to 9, 7.5 to 8.5, 7.9 to 8.5, 8.0 to 8.4 or 8.1 to 8.3.

8. The process of claim 7, wherein the buffer solution has a pH of 8.2.

9. The process of claim 1, wherein the buffering agent is selected from the group consisting of a citrate buffer, an acetate buffer, a succinate buffer and a phosphate buffer or the buffering agent is selected from the group consisting of HEPPSO (N-(2-hydroxyethyl)piperazine-N'-(2-hydroxy-propanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), EPPS (4-(2-hydroxyethyl)piperazine-1-propanesulfonic acid), TES (N-[tris(hydroxymethyl)methyl]-2-aminoethanesulfonic acid), MES (2-(N-morpholino)ethanesulfonic acid) and a combination thereof.

10. The process of claim 1, wherein the buffer solution further comprises sodium chloride.

11. The process of claim 1, wherein the buffer solution further comprises an organic solvent.

12. The process of claim 1, wherein molar excess amount of the cytotoxic agent relative to the bifunctional crosslinking reagent is used in the reaction of step (a).

13. The process of claim 1, wherein the solution in step (b) has a pH of 5.0-9.0, 5.5-9.0, 6.0-9.0 or 6.5-9.0.

14. The process of claim 1, wherein the solution in step (b) comprises a buffering agent selected from the group consisting of a citrate buffer, an acetate buffer, a succinate buffer and a phosphate buffer, or a buffering agent selected from the group consisting of HEPPSO (N-(2-hydroxyethyl)piperazine-N'-(2-hydroxypropanesulfonic acid)), POPSO (piperazine-1,4-bis(2-hydroxy-propane-sulfonic acid) dehydrate), HEPES (4-(2-hydroxyethyl)piperazine-1-ethanesulfonic acid), EPPS (4-(2-hydroxyethyl)piperazine-1-propanesulfonic acid), TES (N-[tris(hydroxymethyl)methyl]-2-aminoethanesulfonic acid), MES (2-(N-morpholino)ethanesulfonic acid) and a combination thereof.

15. The process of claim 1, wherein the solution in step (b) further comprises an organic solvent.

16. The process of claim 1, wherein concentration of the cell-binding agent in the solution of step (b) is 5 g/L to 100 g/L.

17. The process of claim 1, wherein the molar ratio of the bifunctional crosslinking reagent to the cell-binding agent is from 2 to 10.

18. The process of claim 1, wherein the process further comprises the step of quenching the reaction in step (b) by adjusting the pH of the solution to 5 or below.

19. The process of claim 1, wherein the antibody is selected from huN901, huMy9-6, huB4, huC242, trastuzumab, bivatuzumab, sibrotuzumab, CNTO95, huDS6, rituximab, anti-Her2 antibody, anti-EGFR antibody, anti-CD27L antibody, anti-EGFRvIII antibody, anti-Cripto antibody, anti-CD138 antibody, anti-CD38 antibody, anti-EphA2 antibody, integrin targeting antibody, anti-CD37 antibody, anti-folate receptor antibody, anti-Her3 antibody, and anti-IGF1R antibody.

* * * * *

```
SEQUENCE LISTING

<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Tyr Met Phe Thr Ser Tyr Gly Ile Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Trp Val Ser Thr Tyr Asn Gly Asp Thr Asn Tyr Ala Gln Lys Phe Gln
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Val Leu Gly Tyr Tyr Asp Ser Ile Asp Gly Tyr Tyr Tyr Gly Met Asp
1               5                   10                  15

Val

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Gly Gly Asn Asn Ile Gly Asp Lys Ser Val His
1               5                   10

<210> SEQ ID NO 5
<211> LENGTH: 7
<212> TYPE: PRT
```

```
<213> ORGANISM: Artificial Sequence
<220> FEATURE:
<223> OTHER INFORMATION: Synthetic

<400> SEQUENCE: 5

Leu Asp Thr Glu Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Gln Val Trp Asp Ser Gly Ser Asp His Val Val
1               5                   10

<210> SEQ ID NO 7
<211> LENGTH: 126
<212> TYPE: PRT
<213> ORGANISM: Artificial Sequence
<220> FEATURE:
<223> OTHER INFORMATION: Synthetic

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Thr Ser Tyr
            20                  25                  30

Gly Ile Ser Trp Val Arg Gln Ala Pro Gly Gln Gly Leu Glu Trp Met
        35                  40                  45

Gly Trp Val Ser Thr Tyr Asn Gly Asp Thr Asn Tyr Ala Gln Lys Phe
    50                  55                  60

Gln Gly Arg Val Thr Val Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Val Leu Gly Tyr Tyr Asp Ser Ile Asp Gly Tyr Tyr Tyr Gly
            100                 105                 110

Met Asp Val Trp Gly Gln Gly Thr Thr Val Thr Val Ser Ser
        115                 120                 125

<210> SEQ ID NO 8
<211> LENGTH: 109
<212> TYPE: PRT
<213> ORGANISM: Artificial Sequence
<220> FEATURE:
<223> OTHER INFORMATION: Synthetic

<400> SEQUENCE: 8

Gln Ser Val Leu Thr Gln Pro Pro Ser Leu Ser Val Ala Pro Gly Lys
1               5                   10                  15

Thr Ala Thr Phe Thr Cys Gly Gly Asn Asn Ile Gly Asp Lys Ser Val
            20                  25                  30

His Trp Tyr Arg Gln Lys Pro Gly Gln Ala Pro Val Leu Val Met Tyr
        35                  40                  45

Leu Asp Thr Glu Arg Pro Ser Gly Ile Pro Glu Arg Met Ser Gly Ser
    50                  55                  60

Asn Phe Gly Asn Thr Ala Thr Leu Thr Ile Thr Arg Val Glu Ala Gly
```

```
            65                   70                  75                  80
Asp Glu Ala Asp Tyr Tyr Cys Gln Val Trp Asp Ser Gly Ser Asp His
                    85                  90                  95

Val Val Phe Gly Gly Gly Thr Lys Leu Thr Val Leu Gly
            100                 105

<210> SEQ ID NO 9
<211> LENGTH: 456
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Thr Ser Tyr
                20                  25                  30

Gly Ile Ser Trp Val Arg Gln Ala Pro Gly Gln Gly Leu Glu Trp Met
            35                  40                  45

Gly Trp Val Ser Thr Tyr Asn Gly Asp Thr Asn Tyr Ala Gln Lys Phe
        50                  55                  60

Gln Gly Arg Val Thr Val Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Val Leu Gly Tyr Tyr Asp Ser Ile Asp Gly Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
```

```
                    325                 330                 335
Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
            450                 455

<210> SEQ ID NO 10
<211> LENGTH: 214
<212> TYPE: PRT
<213> ORGANISM: Artificial Sequence
<220> FEATURE:
<223> OTHER INFORMATION: Synthetic

<400> SEQUENCE: 10

Gln Ser Val Leu Thr Gln Pro Pro Ser Leu Ser Val Ala Pro Gly Lys
1               5                   10                  15

Thr Ala Thr Phe Thr Cys Gly Gly Asn Asn Ile Gly Asp Lys Ser Val
            20                  25                  30

His Trp Tyr Arg Gln Lys Pro Gly Gln Ala Pro Val Leu Val Met Tyr
            35                  40                  45

Leu Asp Thr Glu Arg Pro Ser Gly Ile Pro Glu Arg Met Ser Gly Ser
        50                  55                  60

Asn Phe Gly Asn Thr Ala Thr Leu Thr Ile Thr Arg Val Glu Ala Gly
65              70                  75                  80

Asp Glu Ala Asp Tyr Tyr Cys Gln Val Trp Asp Ser Gly Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Ala Glu Cys Ser
        210
```

<210> SEQ ID NO 11
<211> LENGTH: 795
<212> TYPE: PRT
<213> ORGANISM: Homo sapiens

<400> SEQUENCE: 11

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Glu Leu Val
        35                  40                  45

Phe Gly Ser Gly Asp Ala Val Glu Leu Ser Cys Pro Pro Pro Gly Gly
    50                  55                  60

Gly Pro Met Gly Pro Thr Val Trp Val Lys Asp Gly Thr Gly Leu Val
65                  70                  75                  80

Pro Ser Glu Arg Val Leu Val Gly Pro Gln Arg Leu Val Leu Asn Ala
                85                  90                  95

Ser His Glu Asp Ser Gly Ala Tyr Ser Cys Arg Gln Arg Leu Thr Arg
            100                 105                 110

Val Leu Cys His Phe Ser Val Arg Val Thr Asp Ala Pro Ser Ser Gly
        115                 120                 125

Asp Asp Glu Asp Gly Glu Asp Glu Ala Glu Asp Thr Gly Val Asp Thr
    130                 135                 140

Gly Ala Pro Tyr Trp Thr Arg Pro Glu Arg Met Asp Lys Lys Leu Leu
145                 150                 155                 160

Ala Val Pro Ala Ala Asn Thr Val Arg Phe Arg Cys Pro Ala Ala Gly
                165                 170                 175

Asn Pro Thr Pro Ser Ile Ser Trp Leu Lys Asn Gly Arg Glu Phe Arg
            180                 185                 190

Gly Glu His Arg Ile Gly Gly Ile Lys Leu Arg His Gln Gln Trp Ser
        195                 200                 205

Leu Val Met Glu Ser Val Val Pro Ser Asp Arg Gly Asn Tyr Thr Cys
    210                 215                 220

Val Val Glu Asn Lys Phe Gly Ser Ile Arg Gln Thr Tyr Thr Leu Asp
225                 230                 235                 240

Val Leu Glu Arg Ser Pro His Arg Pro Ile Leu Gln Ala Gly Leu Pro
                245                 250                 255

Ala Asn Gln Thr Ala Val Leu Gly Ser Asp Val Glu Phe His Cys Lys
            260                 265                 270

Val Tyr Ser Asp Ala Pro His Ile Gln Trp Leu Lys His Val Glu Val
        275                 280                 285

Asn Gly Ser Lys Val Gly Pro Asp Gly Thr Pro Tyr Val Thr Val Leu
    290                 295                 300

Lys Thr Ala Gly Ala Asn Thr Thr Asp Lys Glu Leu Glu Val Leu Ser
305                 310                 315                 320

Leu His Asn Val Thr Phe Glu Asp Ala Gly Glu Tyr Thr Cys Leu Ala
                325                 330                 335

Gly Asn Ser Ile Gly Phe Ser His His Ser Ala Trp Leu Val Val Leu
            340                 345                 350

Pro Ala Glu Glu Glu Leu Val Glu Ala Asp Glu Ala Gly Ser Val Tyr
        355                 360                 365

Ala Gly Ile Leu Ser Tyr Gly Val Gly Phe Phe Leu Phe Ile Leu Val
    370                 375                 380

```
Val Ala Ala Val Thr Leu Cys Arg Leu Arg Ser Pro Pro Lys Lys Gly
385                 390                 395                 400

Leu Gly Ser Pro Thr Val His Lys Ile Ser Arg Phe Pro Leu Lys Arg
            405                 410                 415

Gln Val Ser Leu Glu Ser Asn Ala Ser Asn Ser Ser Asn Thr Pro Leu
        420                 425                 430

Val Arg Ile Ala Arg Leu Ser Ser Gly Glu Gly Pro Thr Leu Ala Asn
            435                 440                 445

Val Ser Glu Leu Glu Leu Pro Ala Asp Pro Lys Trp Glu Leu Ser Arg
        450                 455                 460

Ala Arg Leu Thr Leu Gly Lys Pro Leu Gly Glu Gly Cys Phe Gly Gln
465                 470                 475                 480

Val Val Met Ala Glu Ala Ile Gly Ile Asp Lys Asp Arg Ala Ala Lys
            485                 490                 495

Pro Val Thr Val Ala Val Lys Met Leu Lys Asp Asp Ala Thr Asp Lys
        500                 505                 510

Asp Leu Ser Asp Leu Val Ser Glu Met Glu Met Met Lys Met Ile Gly
            515                 520                 525

Lys His Lys Asn Ile Ile Asn Leu Leu Gly Ala Cys Thr Gln Gly Gly
        530                 535                 540

Pro Leu Tyr Val Leu Val Glu Tyr Ala Ala Lys Gly Asn Leu Arg Glu
545                 550                 555                 560

Phe Leu Arg Ala Arg Arg Pro Pro Gly Leu Asp Tyr Ser Phe Asp Thr
            565                 570                 575

Cys Lys Pro Pro Glu Glu Gln Leu Thr Phe Lys Asp Leu Val Ser Cys
        580                 585                 590

Ala Tyr Gln Val Ala Arg Gly Met Glu Tyr Leu Ala Ser Lys Cys Ile
            595                 600                 605

His Arg Asp Leu Ala Ala Arg Asn Val Leu Val Thr Glu Asp Asn Val
        610                 615                 620

Met Lys Ile Ala Asp Phe Gly Leu Ala Arg Asp Val His Asn Leu Asp
625                 630                 635                 640

Tyr Tyr Lys Lys Thr Thr Asn Gly Arg Leu Pro Val Lys Trp Met Ala
            645                 650                 655

Pro Glu Ala Leu Phe Asp Arg Val Tyr Thr His Ser Asp Val Ser Phe
        660                 665                 670

Gly Val Leu Leu Trp Glu Ile Phe Thr Leu Gly Gly Ser Pro Tyr Pro
            675                 680                 685

Gly Ile Pro Val Glu Glu Leu Phe Lys Leu Leu Lys Glu Gly His Arg
        690                 695                 700

Met Asp Lys Pro Ala Asn Cys Thr His Asp Leu Tyr Met Ile Met Arg
705                 710                 715                 720

Glu Cys Trp His Ala Ala Pro Ser Arg Pro Thr Phe Lys Leu Val Glu
            725                 730                 735

Asp Leu Asp Arg Val Leu Thr Val Thr Ser Thr Asp Glu Tyr Leu Asp
        740                 745                 750

Leu Ser Ala Pro Phe Glu Tyr Ser Pro Gly Gly Gln Asp Thr Pro Ser
            755                 760                 765

Ser Ser Ser Ser Gly Asp Asp Ser Val Phe Ala His Asp Leu Leu Pro
        770                 775                 780

Pro Ala Pro Pro Ser Ser Gly Gly Ser Arg Thr
785                 790                 795
```